US010485544B2

(12) United States Patent
Shelton, IV et al.

(10) Patent No.: US 10,485,544 B2
(45) Date of Patent: Nov. 26, 2019

(54) END EFFECTOR HAVING EXTENSION FEATURES FOR MATING WITH ADJUNCTS

(71) Applicant: Ethicon LLC, Guaynabo, PR (US)

(72) Inventors: Frederick E. Shelton, IV, Hillsboro, OH (US); Prudence Vulhop, Cincinnati, OH (US); Jason L. Harris, Lebanon, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 373 days.

(21) Appl. No.: 15/435,969

(22) Filed: Feb. 17, 2017

(65) Prior Publication Data
US 2018/0235621 A1    Aug. 23, 2018

(51) Int. Cl.
*A61B 17/03* (2006.01)
*A61B 17/064* (2006.01)
*A61B 17/072* (2006.01)
*A61B 17/115* (2006.01)
*A61B 17/00* (2006.01)

(52) U.S. Cl.
CPC .. *A61B 17/07207* (2013.01); *A61B 17/00491* (2013.01); *A61B 17/07292* (2013.01); *A61B 17/1155* (2013.01); *A61B 2017/00004* (2013.01); *A61B 2017/0023* (2013.01); *A61B 2017/00889* (2013.01); *A61B 2017/00893* (2013.01); *A61B 2017/07257* (2013.01); *A61B 2017/07264* (2013.01);
(Continued)

(58) Field of Classification Search
CPC ...... A61B 17/07292; A61B 2017/0004; A61B 2017/0406
See application file for complete search history.

(56) References Cited

U.S. PATENT DOCUMENTS 5,542,594 A * 8/1996 McKean .......... A61B 17/07207
                                                    227/178.1
7,143,925 B2  12/2006 Shelton, IV et al.
(Continued)

FOREIGN PATENT DOCUMENTS

EP    2008595 A2   12/2008
EP    2462880 A2    6/2012
(Continued)

*Primary Examiner* — Andrew M Tecco
*Assistant Examiner* — Eyamindae C Jallow
(74) *Attorney, Agent, or Firm* — Mintz Levin Cohn Ferris Glovsky and Popeo, P.C.

(57) ABSTRACT

An end effector for a surgical instrument is provided that has a first jaw, such as a cartridge body, having on a tissue-contacting surface thereof a plurality of staple cavities configured to seat staples therein, and a second jaw, such as an anvil, with a plurality of staple forming cavities formed on a tissue-contacting surface thereof. The first jaw has a generally rectangular nominal perimeter defining a regular perimeter around outer rows of the plurality of staple cavities. At least one of the first and second jaws has extension elements extending beyond the nominal perimeter of that jaw such that each of the extension elements has at least one attachment feature formed thereon. An adjunct material having a shape complementary to a shape of the jaw is configured to releasably mate with the attachment features formed on the jaw, via corresponding adjunct's mating features.

19 Claims, 8 Drawing Sheets

(52) U.S. Cl.
CPC ............... *A61B 2017/07271* (2013.01); *A61B 2017/07278* (2013.01); *A61B 2017/07285* (2013.01)

(56) References Cited

U.S. PATENT DOCUMENTS

| | | | |
|---|---|---|---|
| 7,601,118 B2 | 10/2009 | Smith et al. | |
| 8,028,883 B2 * | 10/2011 | Stopek | A61B 17/072 227/175.1 |
| 8,317,070 B2 | 11/2012 | Hueil et al. | |
| 8,393,514 B2 | 3/2013 | Shelton, IV et al. | |
| 8,584,920 B2 * | 11/2013 | Hodgkinson | A61B 17/0682 227/175.1 |
| 8,814,025 B2 * | 8/2014 | Miller | A61B 17/00491 227/180.1 |
| 9,282,962 B2 | 3/2016 | Schmid et al. | |
| 9,433,420 B2 * | 9/2016 | Hodgkinson | A61B 17/07207 |
| 2002/0165559 A1 * | 11/2002 | Grant | A61B 17/07207 606/139 |
| 2012/0241499 A1 | 9/2012 | Chester et al. | |
| 2013/0256377 A1 | 10/2013 | Schmid et al. | |
| 2014/0048580 A1 * | 2/2014 | Merchant | A61B 17/064 227/176.1 |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 * | 5/2015 | Shelton, IV | A61B 17/07292 623/23.72 |
| 2015/0134077 A1 | 5/2015 | Shelton, IV et al. | |
| 2015/0272575 A1 | 10/2015 | Leimbach et al. | |
| 2015/0277471 A1 | 10/2015 | Leimbach et al. | |
| 2015/0351758 A1 | 12/2015 | Shelton, IV et al. | |
| 2016/0030043 A1 * | 2/2016 | Fanelli | A61B 17/07207 227/175.1 |
| 2016/0089142 A1 | 3/2016 | Harris et al. | |
| 2017/0055986 A1 | 3/2017 | Harris et al. | |

FOREIGN PATENT DOCUMENTS

| | | |
|---|---|---|
| EP | 2700367 A1 | 2/2014 |
| EP | 2870932 A2 | 5/2015 |
| WO | 97/01989 A1 | 1/1997 |

* cited by examiner

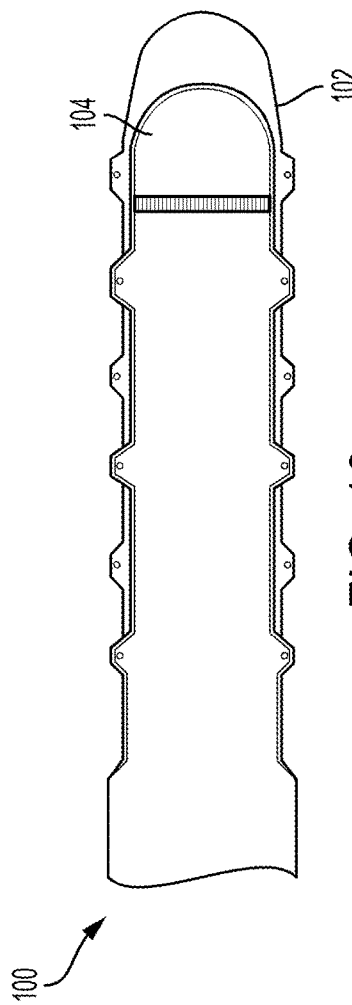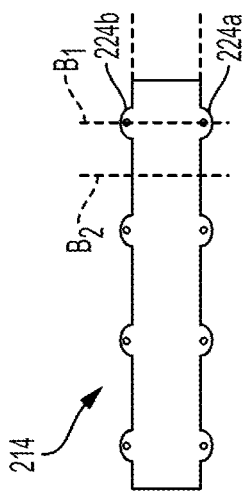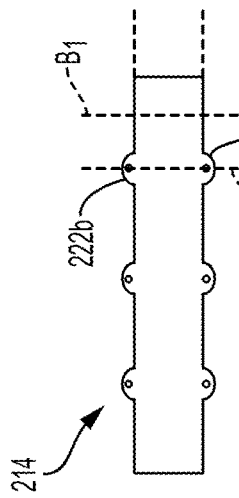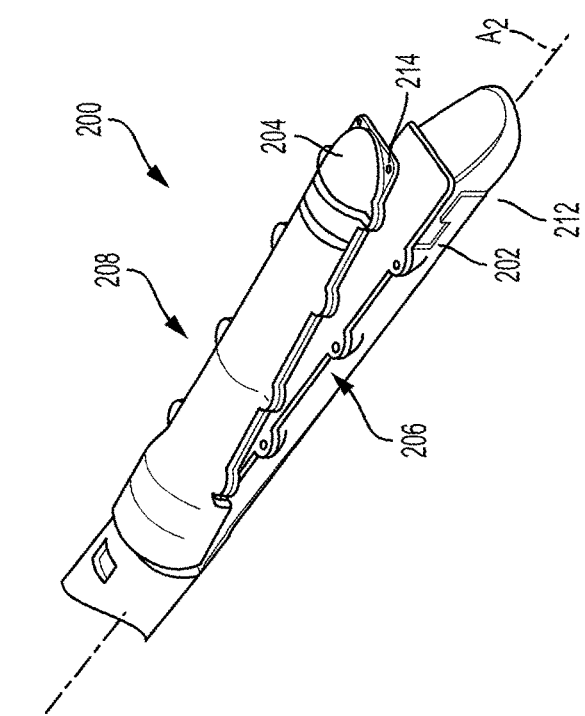

END EFFECTOR HAVING EXTENSION FEATURES FOR MATING WITH ADJUNCTS

The present disclosure relates generally to techniques for releasably retaining an adjunct material on at least one jaw of an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

In one aspect, an end effector for a surgical instrument is provided that in some implementations includes a first jaw having a cartridge body having on a tissue-contacting surface thereof a plurality of staple cavities configured to seat staples therein, a second jaw having an anvil with a plurality of staple forming cavities formed on a tissue-contacting surface thereof, a plurality of attachment features formed on at least one jaw of the first and second jaws, and an adjunct material. At least one of the first and second jaws is movable relative to the other between open and closed positions. The first jaw has a generally rectangular nominal perimeter defining a regular perimeter around outer rows of the plurality of staple cavities. The second jaw has a generally rectangular nominal perimeter opposed to the nominal perimeter of the first jaw. The plurality of attachment features are formed on the at least one jaw of the first and second jaws on extension elements extending beyond the nominal perimeter of the at least one jaw such that each of the extension elements has at least one attachment feature formed thereon. The adjunct material has a shape complementary to at least one of the first and second jaws and being configured to releasably mate with the attachment features.

The end effector can vary in many different ways. For example, the cartridge body can be a removable and replaceable cartridge body. As another example, in some implementations, the extension elements are formed along at least one of the long sides of the at least one jaw. The at least one attachment feature can be a projection extending perpendicular to a longitudinal axis of the at least one jaw from the corresponding extension element formed on the at least one jaw. The adjunct material has at least one mating feature that is complementary to the at least one attachment feature and is configured to releasably mate with the at least one attachment feature. In some implementations, the at least one attachment feature is in the form of a projection extending perpendicular to a longitudinal axis of the at least one jaw from the corresponding extension element formed on the at least one jaw, and the at least one mating feature is in the form of a through opening formed in the adjunct material and configured to receive the projection therein.

The extension elements extending beyond the nominal perimeter of the at least one jaw can extend in a plane of the at least one jaw that is parallel to a tissue contacting surface of the at least one jaw. In some implementations, the extension elements are formed integrally with the at least one jaw.

The extension elements extending beyond the nominal perimeter of the at least one jaw can include first extension elements formed on the first jaw and second extension elements formed on the second jaw. The first and second extension elements can be formed such that, when the end effector is in the closed position, the first extension elements extend beyond the nominal perimeter of the second jaw and the second extension elements extend beyond the nominal perimeter of the first jaw. The first extension elements can be staggered with respect to the second extension elements.

In some implementations, the other one of the first and second jaws has at least one second attachment feature formed thereon that is different from each of the attachment features formed on the extension elements extending beyond the nominal perimeter of the at least one jaw. The at least one second attachment feature is configured to mate with a second adjunct material to releasably retain the second adjunct material on the other jaw.

In some implementations, the at least one attachment feature can be a recess formed in the corresponding extension element formed on the at least one jaw. In other implementations, the at least one attachment feature can be a through opening formed in the corresponding extension element formed on the at least one jaw.

In another aspect, an adjunct configured to be releasably retained on a jaw of an end effector for a surgical instrument is provided that in some implementations has a generally rectangular nominal perimeter with discrete extension elements that extend beyond the nominal perimeter in a plane parallel to a surface of the adjunct configured to contact tissue, at least two of the extension elements being formed along each of long sides of the nominal perimeter and cause a shape of the adjunct to deviate from a shape of the generally rectangular nominal perimeter. The adjunct can also have a plurality of mating features for releasably retaining the adjunct on the jaw, each of the mating features being disposed on a corresponding extension element.

The adjunct can vary in many different ways. For example, the mating features can be in the form of openings. As another example, the extension elements can be formed integrally with the adjunct.

BRIEF DESCRIPTION OF DRAWINGS

This disclosure will be more fully understood from the following detailed description taken in conjunction with the accompanying drawings, in which:

FIG. 10 is a top view of the end effector of FIG. 6, showing the jaws of the end effector in a closed position;

FIG. 11 is a perspective view of another embodiment of an end effector in accordance with the described techniques;

FIG. 12 is a top view of the adjunct material releasably retained on the anvil of the end effector of FIG. 11;

FIG. 13 is a top view of the adjunct material releasably retained on the cartridge of the end effector of FIG. 11;

DETAILED DESCRIPTION

Figure 1:
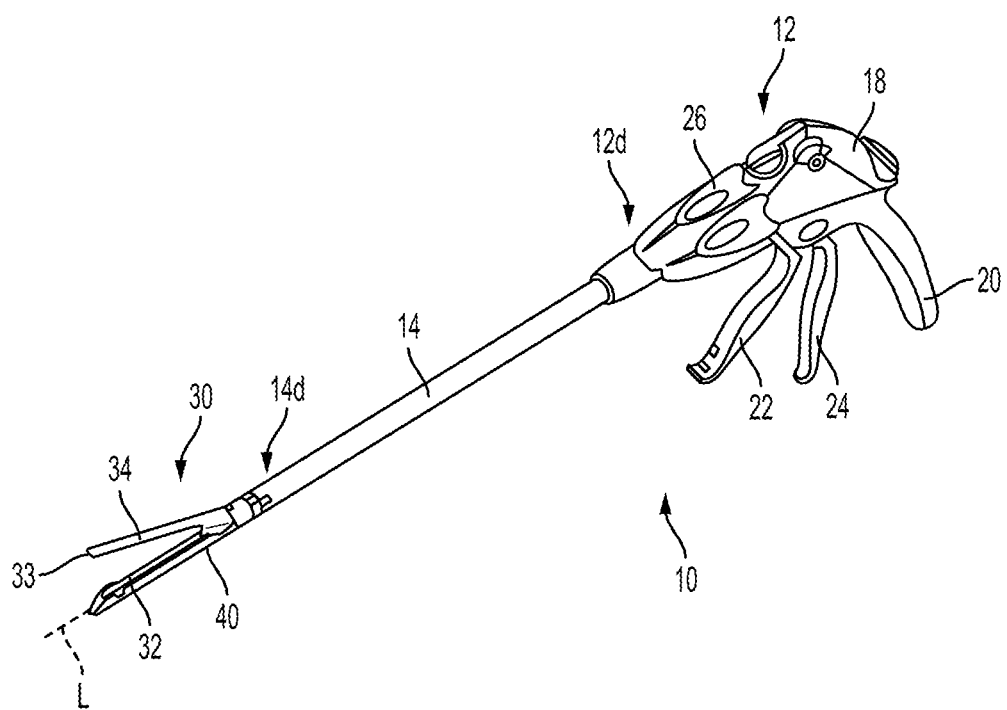
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts" or "buttresses," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) or buttress(es) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used on a variety of tissues in a variety of different surgical procedures, for example in thoracic surgery or in gastric surgery.

Figure 2:
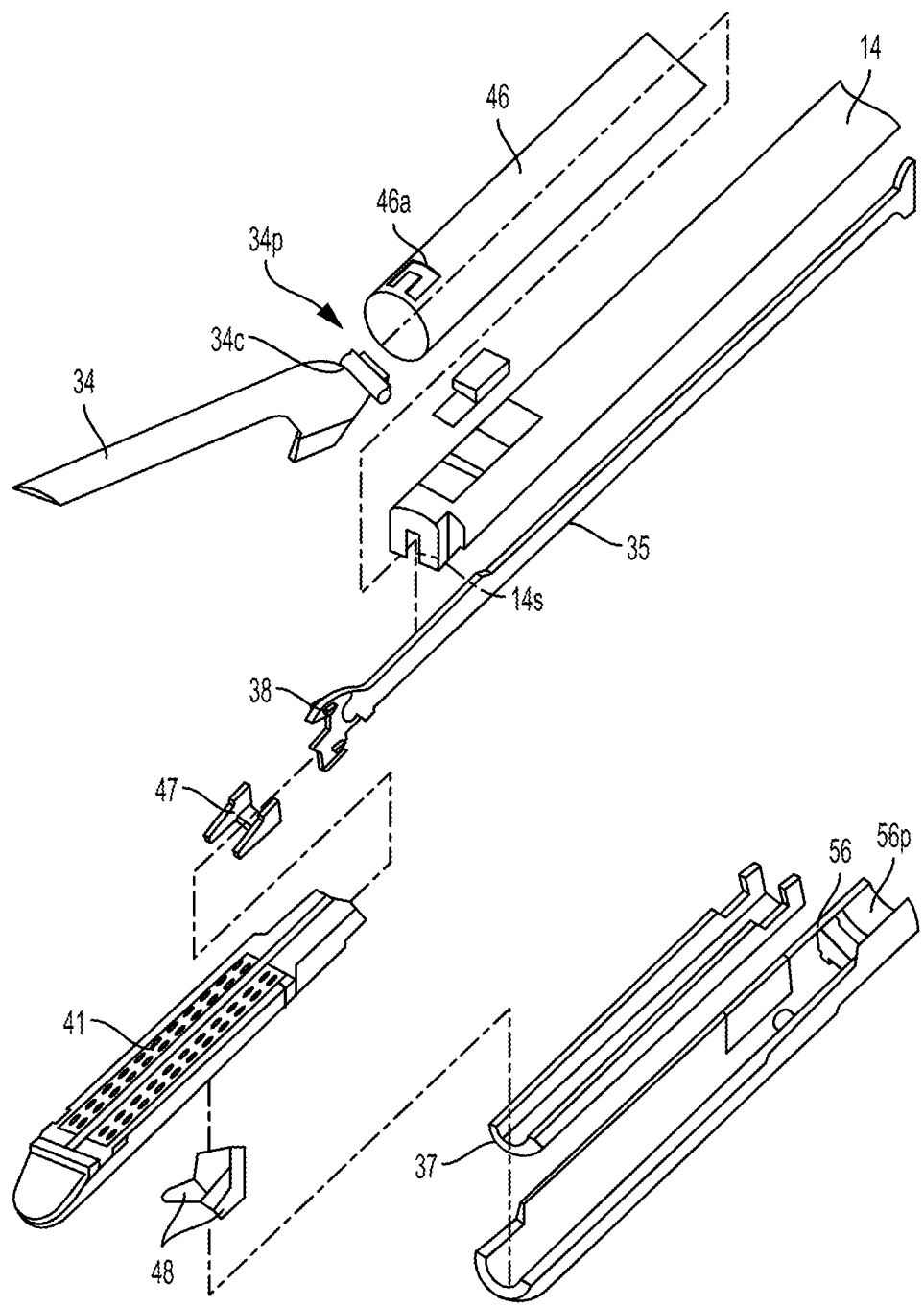
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
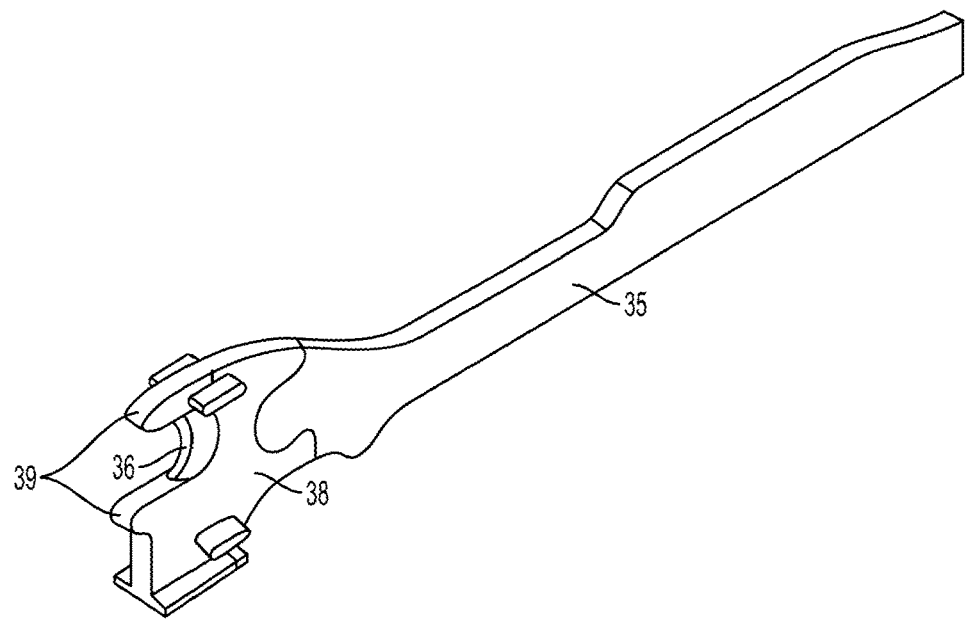
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
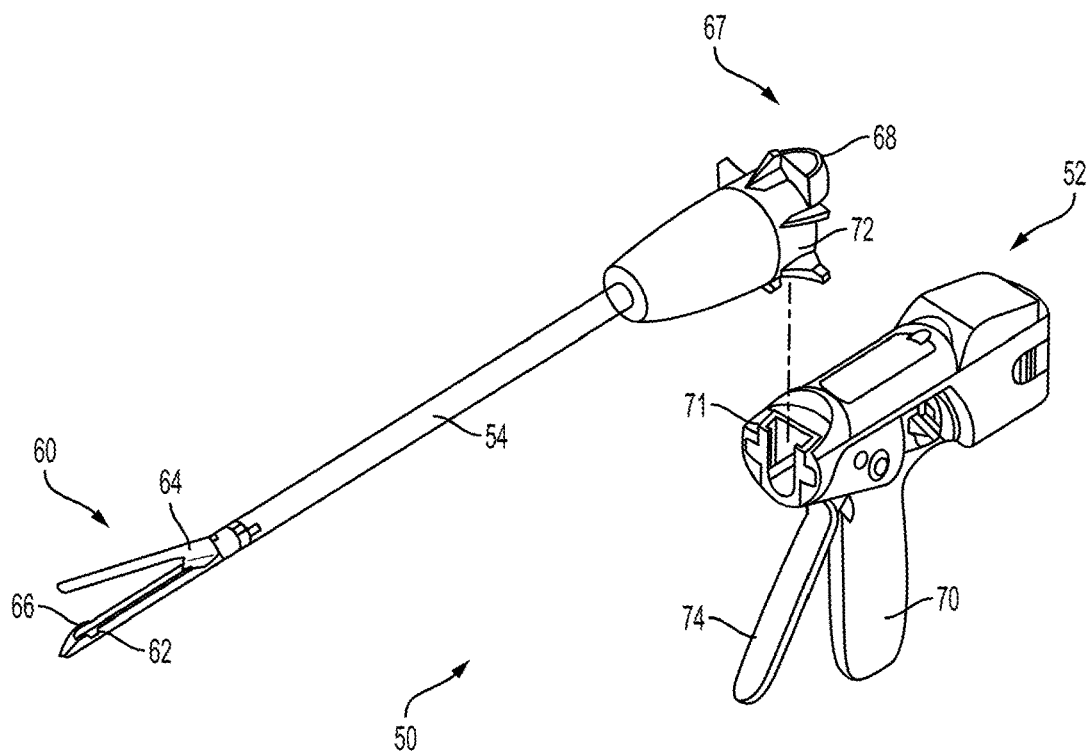
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
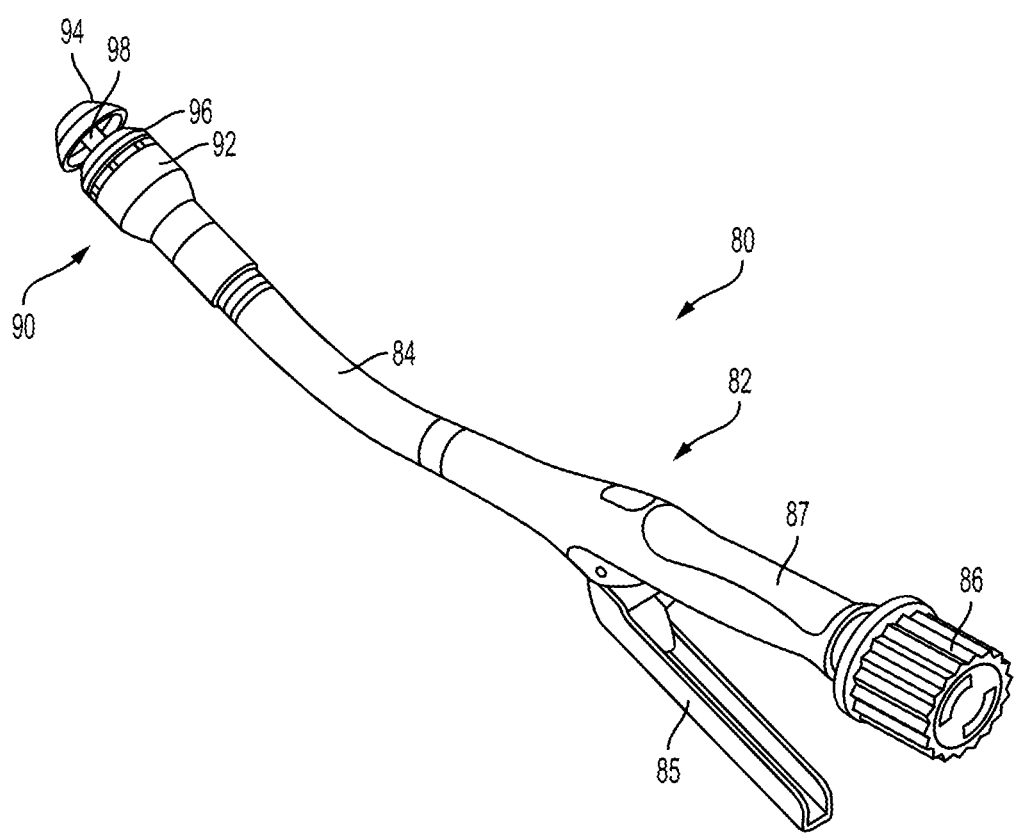
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be made from a film formed from any suitable material or a combination of materials discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers.

An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjunct that has a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Implementations

Various exemplary techniques for releasably retaining an adjunct material on one or both jaws of an end effector of a surgical instrument are described herein. One or both of the opposed jaws can have extension elements formed thereon that extend beyond a nominal perimeter of that jaw. The extension elements are formed outside an area of the jaw's tissue-contacting and treating surface having staple-holding cavities (if the jaw is a cartridge body) or a tissue-contacting surface having staple-forming cavities (if the jaw is an anvil). An adjunct material configured to be releasably retained on the jaw can have a shape complementary to that of the jaw.

In some implementations, an end effector for a surgical instrument has first and second jaws, at least one of which is movable relative to the other one between open and closed positions. For example, the first jaw can have a cartridge body having on a tissue-contacting surface thereof a plurality of staple cavities configured to seat staples therein. The first jaw can have a generally rectangular nominal perimeter defining a regular perimeter around outer rows of the plurality of staple cavities. The second jaw can have or can be an anvil with a plurality of staple forming cavities formed on a tissue-contacting surface thereof. The second jaw can also have a generally rectangular nominal perimeter opposed to the nominal perimeter of the first jaw.

At least one of the first and second jaws can have a plurality of attachment features formed thereon on extension elements extending beyond the nominal perimeter of the at least one jaw. Each of the extension elements can have at least one attachment feature formed thereon. For example, the attachment feature can be a projection extending from the corresponding extension element. The attachment feature is configured to mate with a corresponding mating feature formed on an adjunct material that has a shape complementary to a shape of the jaw.

FIGS. 6, 7, 8, and 9 illustrate an example of an end effector 100 of a surgical instrument configured to be coupled to a distal end of an elongate shaft of the surgical instrument (not shown). The end effector 100 has a first jaw in the form a cartridge body 102 and a second opposed jaw in the form of an anvil 104 that are configured to clamp tissue therebetween. At least one of the cartridge body 102 and the anvil 104 is movable relative to the other between open and closed positions. In some embodiments, the cartridge body 102 can seat therein a removable and replaceable cartridge. Furthermore, in some embodiments, the cartridge body 102 can be part of a disposable loading unit coupled distally to an elongate shaft of a surgical instrument. One or both of the jaws of the end effector can have an implantable adjunct material releasably retained thereon. For example, the cartridge body 102 can have an adjunct material 101 shown in FIG. 9 releasably retained thereon as discussed in more detail below.

Figure 6:
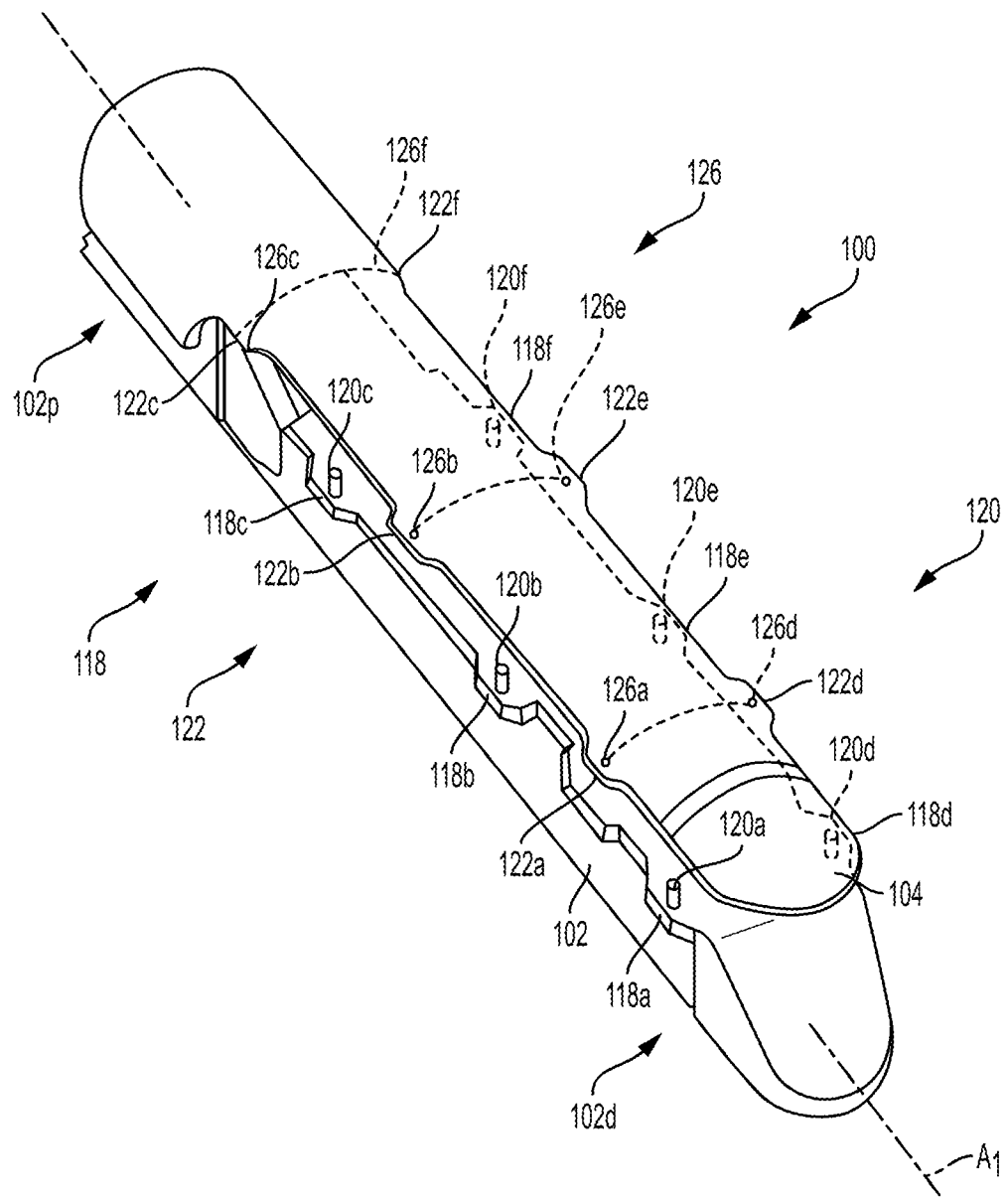
FIG. 6 is a perspective view of one embodiment of an end effector in accordance with the described techniques.
Figure 7:
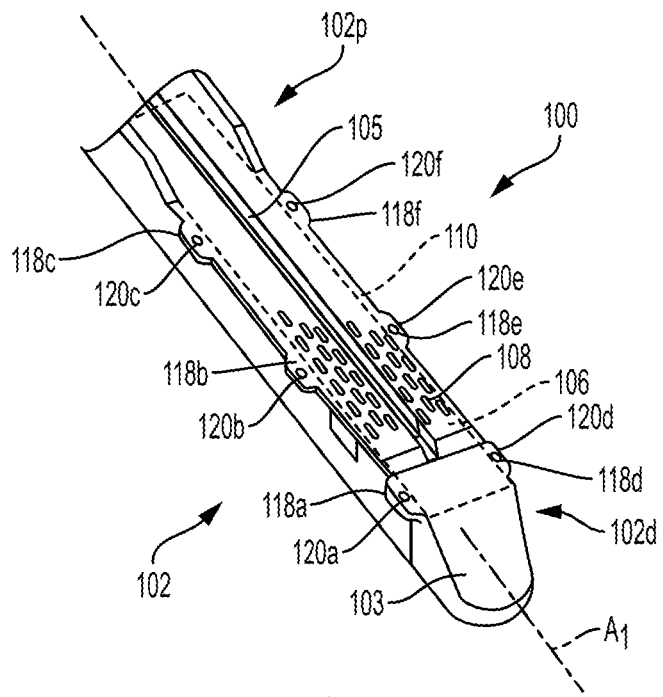
FIG. 7 is a perspective view of the cartridge body of the end effector of FIG. 6.

The cartridge body 102 has a tissue-contacting surface 106 having a plurality of staple cavities 108 (shown partially in FIGS. 7 and 8) configured to seat staples therein. The tissue-contacting surface 106 can have an adjunct material disposed thereon and may therefore not directly contact tissue. Moreover, the tissue-contacting surface 106 is also a tissue-treating surface. The anvil 104 has a plurality of staple forming cavities formed on a tissue-contacting (and treating) surface thereof, which are obscured in FIG. 6. In this example, both the cartridge body 102 and the anvil 104 are generally rectangular. As schematically shown in FIG. 7, the cartridge body 102 has a longitudinal axis Al and a generally rectangular nominal perimeter 110 defining a regular perimeter around outer rows of the plurality of staple cavities 108. The nominal perimeter 110 has long sides 112a, 112b extending along the longitudinal axis A and short sides 114a, 114b. The anvil 104 can also have a generally rectangular nominal perimeter opposed to the nominal perimeter 114 of the cartridge body 102.

In the example illustrated, the cartridge body 102 has multiple extension elements 118 extending beyond the nominal perimeter 110. In particular, as shown in FIG. 6, the extension elements 118 protrude from the cartridge body 102 such that they extend beyond the side walls of the cartridge body 102, such as a sidewall 115 in FIGS. 6-8. As shown, the extension elements 118 are formed outside the area of the cartridge body 102 having the staple holding cavities 108. In this example, six extension elements 118a, 118b, 118c, 118d, 118e, 118f are shown formed on the cartridge body 102. As shown in FIG. 7, the extension elements 118 are formed along at least one of the long sides 112a, 112b of the nominal perimeter 114, in the plane of the tissue-contacting surface 106 of the cartridge body 102. In embodiments in which the cartridge body 102 is in the form of a channel configured to removably and replaceably sit therein a cartridge with staples, the extension elements are formed on a body of the channel. In embodiments in which the entire cartridge body 102 is removable and replaceable (e.g., as part of a disposable loading unit), the extension elements are formed on the cartridge body 102.

As shown, the distal-most extension elements 118a, 118d are formed on opposite sides from a knife channel 105 (FIG. 7) at a distal end 102d of the cartridge body 102, adjacent to a distal tip 103. The extension elements 118b, 118e are formed more proximally on both sides of the knife channel 105, and the extension elements 118d, 118f are the closest to the proximal end 102p of the cartridge body 102. In this example, the pairs of extension elements formed at opposed sides from the knife channel 105 (e.g., the extension elements 118a, 118d) can be disposed along the same axis, which can be perpendicular to the longitudinal axis Al of the jaw 102. The extension elements formed along the same side of the jaw can be spaced equidistantly from one another along the side of the jaw, or one or more of the extension elements can be spaced differently from other extension elements.

The extension elements 118 can have a number of different configurations. In the example illustrated, the extension elements 118 have a trapezoidal shape (e.g., of an isosceles trapezoid) with its longer base being the closest to the nominal perimeter of the cartridge body 102. However, it should be appreciated that the extension elements formed on the cartridge body can be rectangular, square, semi-circular, or they can have any other suitable shape(s), including regular and irregular shapes. Also, the cartridge body can have extension elements of two or more different configurations and/or sizes.

Furthermore, six extension elements 118a, 118b, 118c, 118d, 118e, 118f are shown by way of example only, as any suitable number of extension elements can extend beyond the nominal perimeter of the cartridge body. For example, one, two, three, four, five, or greater than six extension elements can be formed. Also, a different number of extension elements can be formed on one long side 112a of the cartridge body 102 as compared to the cartridge body's another long side 112b.

Figure 8:
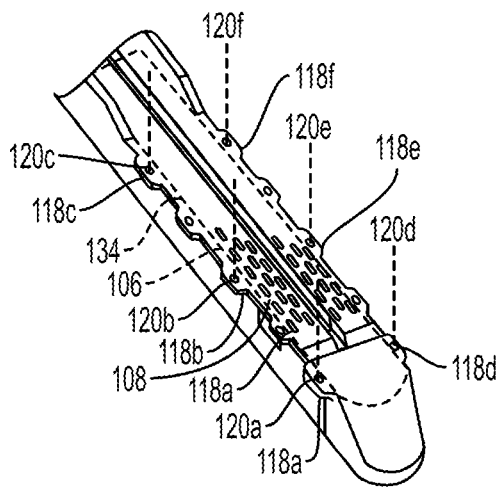
FIG. 8 is another perspective view of the cartridge body of the end effector of FIG. 6.

As in the implementation shown in FIGS. 6-8, the extension elements can be formed in the plane that is parallel to the tissue-contacting surface 106 of the cartridge body 102. However, in other implementations, one or more of the extension elements can have at least a portion thereof formed at an angle to the tissue-contacting surface 106 of the cartridge body 102, in a manner that does not interfere with proper operation of the end effector. The extension elements 118a, 118b, 118c, 118d, 118e, 118f can be formed monolithically and/or integrally with the cartridge body 102. Furthermore, in some embodiments, the extension elements can be separate features coupled to the cartridge body 102 in a suitable way.

The cartridge body 102 and the extension elements 118 have a size such that the cartridge body 102 with the cartridge body 102 with the extension elements 118 extending therefrom fit within a trocar providing access to a surgical site. For example, in the illustrated embodiments, the cartridge body 102 with the extension elements 118 is sized such that the end effector 100 has an overall diameter smaller than 12.8 mm. As a person skilled in the art will appreciate, regardless of the specific configuration of the cartridge body or anvil, the extension elements are formed thereon such that the end effector can fit within a suitable surgical site access instrument.

As shown in FIGS. 6-8, the extension elements 118a, 118b, 118c, 118d, 118e, 118f have respective attachment features 120 formed thereon. In this example, each of the extension elements 118a, 118b, 118c, 118d, 118e, 118f has a respective one of the attachment features 120a, 120b, 120c, 120d, 120e, 120f formed thereon. Each of the attachment features can be in the form of a post or a projection extending from a respective extension element perpendicular to the longitudinal axis Al of the cartridge body 102. The projection can have a rounded tip or a tip having other suitable configuration. However, it should be appreciated that the attachment features formed on the extension elements 118 can have any other various configurations. Also, in some implementations, the jaw (e.g., the cartridge body 102) can have attachment features of more than one type formed thereon.

One or both of the cartridge body 102 and anvil 104 can have an adjunct material (or "adjunct") releasably retained thereon. In the illustrated implementation, the adjunct material has a shape complementary to a shape of the jaw on which it is mounted and the adjunct material is configured to releasably mate with the attachment features formed on the extension elements of the jaw. Thus, the adjunct has a generally rectangular nominal perimeter with discrete extension elements that extend beyond the nominal perimeter in a plane parallel to a surface of the adjunct configured to contact tissue. The extension elements can be formed on the adjunct such that at least two extension elements are formed along each of long sides of the adjunct's nominal perimeter. Each of the extension elements can have at least one mating feature configured to mate with a respective attachment features formed on the jaw.

Figure 9:
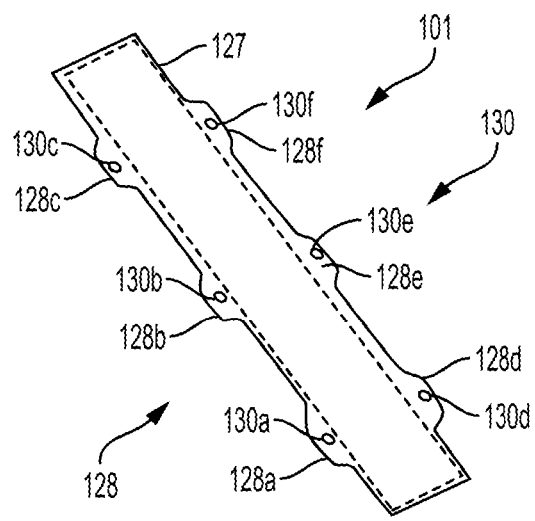
FIG. 9 is a perspective view of the adjunct material releasably retained on at least one jaw of the end effector of FIG. 6.

FIG. 9 shows the adjunct material 101 that can be releasably retained on the tissue-contacting surface 106 of the cartridge body 102. As shown in FIG. 9, the adjunct material 101 has a shape that corresponds to the shape of the cartridge body 102—extension elements 128, such as elements 128a, 128b, 128c, 128d, 128e, 128f are formed that extend beyond a nominal perimeter 127 in a plane parallel to a surface of the adjunct 101 configured to contact tissue. The extension elements 128 can be formed integrally with the adjunct material 101 or they can be separate elements coupled to the adjunct 101 along the nominal perimeter 127 thereof in a suitable manner.

The extension elements 128a, 128b, 128c, 128d, 128e, 128f are configured to be disposed over the respective extension elements 118a, 118b, 118c, 118d, 118e, 118f extending beyond the nominal perimeter 110 of the cartridge body 102. Thus, the shape of the adjunct 101 is such that it "traces" the shape of the cartridge body 102. The size of the adjunct material 101 also corresponds to the size of the cartridge body 102. In this way, the adjunct material 101 is aligned with the cartridge body 102 when the adjunct 101 is disposed thereon.

The adjunct material 101 can be configured to mate with the cartridge body 102 in a variety of different ways. In the example illustrated, as shown in FIG. 9, the adjunct material 101 has a plurality of mating features 130, such as mating features 130a, 130b, 130c, 130d, 130e, 130f that are complementary to the attachment features 120a, 120b, 120c, 120d, 120e, 120f formed on the cartridge body 102 and are configured to releasably mate with the attachment features 120a, 120b, 120c, 120d, 120e, 120f. In the illustrated implementation, the mating features are in the form of through openings formed in the adjunct material 101. The openings are configured so as to receive the projections therein, such that the adjunct material can be released from the engagement with the jaw when staples are ejected from staple cavities.

The mating features 130a, 130b, 130c, 130d, 130e, 130f are formed on the adjunct's extension elements 128a, 128b, 128c, 128d, 128e, 128f as shown in FIG. 9, at locations on these extension elements corresponding to the locations of the cartridge's attachment features 120a, 120b, 120c, 120d, 120e, 120f. In this way, when the adjunct material 101 is superimposed over the cartridge body 102, the mating features 130a, 130b, 130c, 130d, 130e, 130f align with the cartridge's attachment features 120a, 120b, 120c, 120d, 120e such that each opening receives therein a corresponding projection. The cartridge's attachment features and adjunct's mating features can releasably mate via a friction fit or in other ways.

As shown in FIG. 6 illustrating a partially transparent view of the anvil 104, the anvil 104 can also have extension elements 122, such as elements 122a, 122b, 122c, 122d, 122e, 122f, formed thereon that beyond the nominal perimeter 124 thereof. Each of the extension elements 122 can have a shape and size similar to that of the extension elements 118 formed on the cartridge body 102. For example, as illustrated, the extension elements 122 can be generally trapezoidal, though they can have other shapes, as the described techniques are not limited in this respect. Similar to the cartridge body 102, each of the extension elements 122 can have a respective attachment feature 126 thereon for mating with an adjunct to be releasably retained on the anvil 104. FIG. 6 illustrates that each of the extension elements 122a, 122b, 122c, 122d, 122e, 122f can have a respective one of the attachment features 126a, 126b, 126c, 126d, 126e, 126f formed thereon.

In the illustrated implementation, the extension elements 122 are formed on the anvil 104 in a manner such that they do not overlap with the extension elements 118 formed on the cartridge body 102. Thus, as shown in FIG. 6 and additionally in FIG. 8 (where a shadow or footprint 134 of the anvil 104 is schematically shown superimposed over the cartridge body 102), the extension elements 122 are staggered with respect to the extension elements 118.

In the described embodiments, the respective extension elements are formed on the cartridge body 102 and the anvil 104 such that, when the end effector 100 is in the closed position, the cartridge body's extension elements 118 extend beyond the nominal perimeter of the anvil 104 and the anvil's extension elements 122 extend beyond the nominal perimeter of the cartridge body 102. For example, FIG. 10, showing the end effector 100 in a closed configuration, illustrates that the footprint of the cartridge body 102 is outside the footprint of the anvil 104 and that the extension elements 122a, 122b, 122c, 122d, 122e, 122f are staggered with respect to the extension elements 118a, 118b, 118c, 118d, 118e, 118f. However, it should be appreciated that, in some implementations, all or some of the cartridge's and anvil's extension elements are not staggered with respect to one another. For example, the cartridge's and anvil's extension elements can be formed symmetrical, such that at least one of the anvil's extension elements overlaps with at least one of the cartridge's extension elements.

FIG. 11 additionally illustrates an end effector 200 having a longitudinal axis A2, which can have a configuration similar to that of the end effector 100 (FIGS. 6-8 and 10). Thus, similar to the end effector 199, the end effector 200 has extension elements formed, in the example of FIG. 11, on both of the jaws 202 (cartridge body) and 204 (anvil). The extension elements formed on the cartridge body 202 and anvil 204 are collectively identified as extension elements 206, 208, respectively. In this example, each of the cartridge body 202 and anvil 204 releasably retain thereon respective adjunct materials 212, 214 that are separately shown in FIGS. 12 and 13. The cartridge's extension elements 206 and anvil's extension elements 208 have attachment features, such as projections, configured to mate with corresponding mating features (e.g., openings) formed on adjunct materials 212, 214, respectively.

As shown in FIGS. 11-13, the adjunct materials 212, 214 have shapes complementary to shapes of the cartridge body 202 and anvil 204, respectively. In this example, the extension elements 206 formed on the cartridge body 202 are staggered with respect to the extension elements 208 formed on the anvil 204. In a similar manner, the extension elements of the adjunct material 212 are staggered with respect to the extension elements the adjunct material 214. Thus, FIGS. 12 and 13 illustrate that, while the anvil's adjunct material 214 has extension features 224a, 224b along an axis B1 (also shown in FIG. 11), the cartridge body's adjunct material 212 does not have any extension elements formed along the axis B1. However, the cartridge body's adjunct material 212 has extension elements 222a, 222b formed along an axis B2 (also shown in FIG. 11), whereas the anvil's adjunct material 214 does not have extension elements formed along the axis B2.

An implantable adjunct configured to be releasably retained over a jaw of an end effector can be made from a variety of different materials described herein. For example, as discussed above, the adjunct can be formed from one or more of a film, foam, an injection molded thermoplastic, a vacuum thermoformed material, a fibrous structure, and hybrids thereof. The adjunct can also include one or more biologically-derived materials and one or more drugs. Furthermore, in the described implementations, one or more portions of the adjunct can have different properties. For example, the areas configured to be superimposed over the extensions features formed on a jaw can be configured differently from other areas of the adjunct.

A jaw (such as a cartridge body or an anvil) having extension elements and an adjunct material having a shape complementary to that jaw can have other features formed thereon for mating between these components. For example, in some implementations, the jaw can have attachment features in the form of recesses, through openings, or other types of features formed in the corresponding extension elements of the jaw and configured to mate with respective features formed on the adjunct material.

In some implementations, the opposed jaws of the end effector can have different types of adjunct materials releasably retained thereon. Furthermore, the same or different types of adjunct materials can be coupled to the opposed jaws using the same or different techniques. For example, one adjunct material can be attached to one of the jaws via mechanical features (e.g., projections on the jaw and openings on the adjunct, as discussed above), whereas another adjunct material can be attached to the opposed jaw using a suitable adhesive material.

In some embodiments, a cartridge body (e.g., part of a reloadable unit) can have an adjunct material attached thereon via an adhesive material, while another adjunct material can be attached to the anvil using mechanical feature, such as the projections on the jaw and openings on the adjunct. The cartridge body can be manufactured with a suitable adjunct material already retained thereon. At the same time, an adjunct material can be attached to the anvil of an end effector during surgery.

In some implementations, the anvil of an end effector can have mating features in the form of female features formed on the extensions of the anvil extending beyond the anvil's nominal perimeter. The female features, configured to mate with complementary features formed in an adjunct material configured to be releasably retained on the anvil, can be shaped as openings, pockets, cleats, etc. The adjunct material's mating features can be, for example, hooks, snaps, barbs, features having expandable elements (e.g., tree- or umbrella-like features) that can releasably mate with the pocket-type openings in the anvil. Furthermore, in some implementations, the anvil can have one or more three-dimensional pockets that allow an overmold feature of the adjunct to be releasably retained thereon. The overmold feature can be, for example, a projection molded into the three-dimensional pocket. It should be appreciated that at least on of the jaws of the end effector and an adjunct configured to releasably mate with that jaw can also have these features additionally or alternatively to the features described in connection with FIGS. 6-13.

Figure 14:
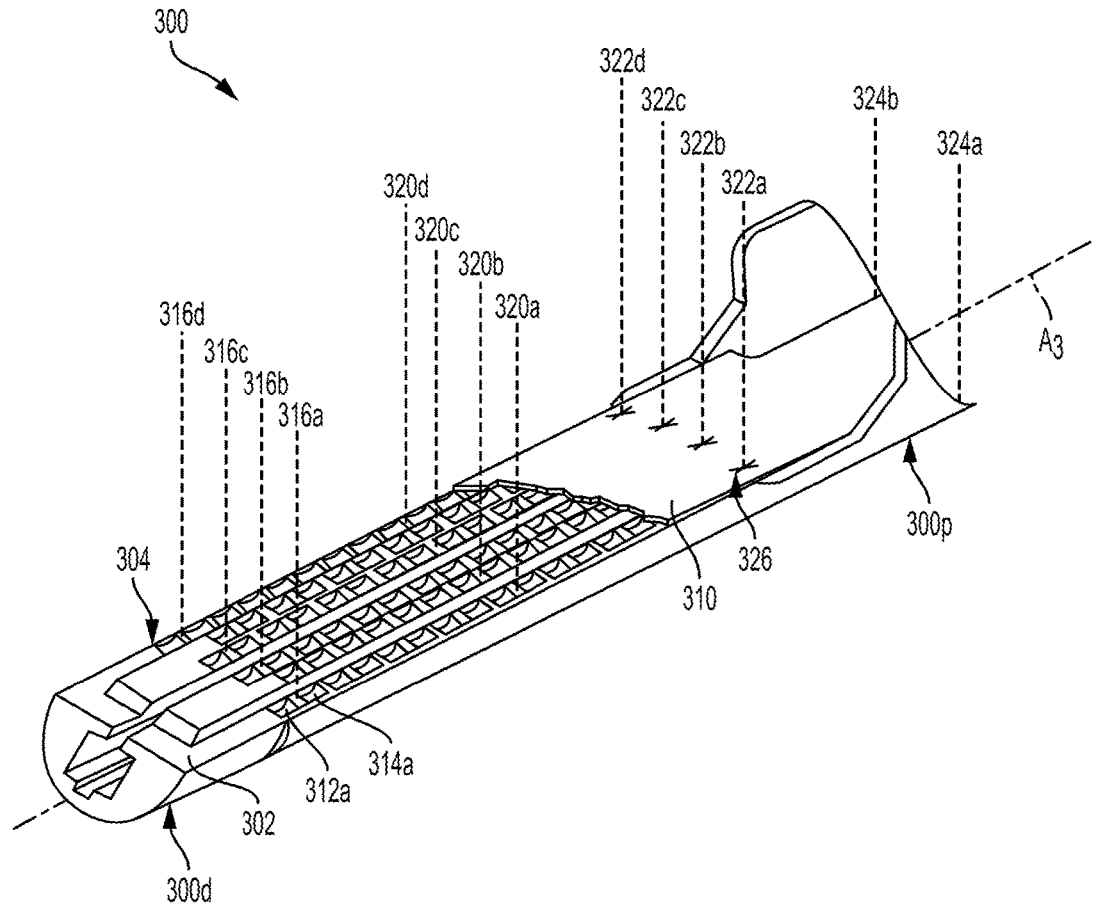
FIG. 14 is a perspective, partially cut-away view of one embodiment of an anvil of an end effector in accordance with the described techniques.
Figure 15:
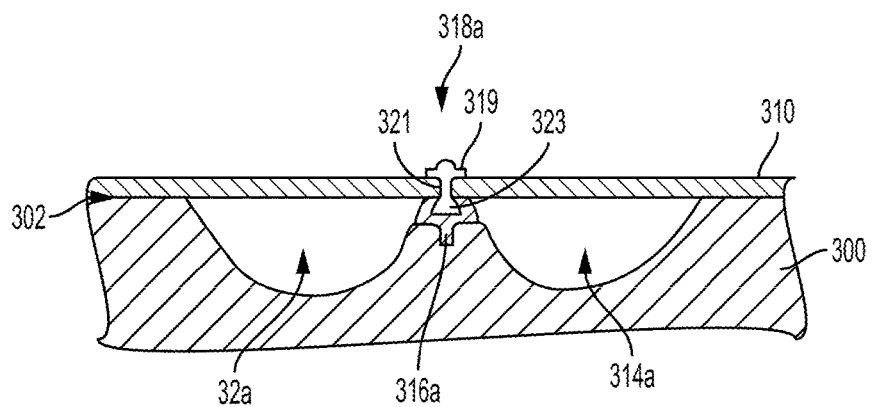
FIG. 15 is a side view of a portion of the anvil of FIG. 14.

Furthermore, in some embodiments, one or both of the jaws of the end effector may not have extension features formed thereon. In such embodiments, attachment features can be formed on an end effector's jaw within a nominal perimeter of the jaw. FIGS. 14 and 15 illustrate an example of such an embodiment providing an anvil 300 of an end effector having female features formed thereon for mating with an adjunct material 310 that has corresponding mating features. The anvil 300 has a tissue-contacting surface 302 having a plurality of staple-forming pockets or cavities 304. The staple-forming cavities 304 can form various patterns on the tissue-contacting surface 302. In this example, the staple-forming cavities 304 are arranged in six rows extending along a longitudinal axis A3 of the anvil 300. As shown in FIG. 14, the tissue-contacting surface 302 has attachment features 316a, 316b, 316c, 316d formed at a distal end 300d of the anvil 300 between adjacent staple-forming cavities. As shown, in this example, the attachment features 316a, 316b, 316c, 316d are formed in a row that is generally perpendicular to a longitudinal axis A3 of the anvil 300.

FIG. 15 illustrates by way of example two adjacent staple-forming cavities 312a, 314a having the attachment feature 316a therebetween, which is in the form of an overmold cleat or pocket. Thus, the attachment feature 316a and other similar attachment features are formed on the anvil's tissue-contacting surface 302 by overmolding a suitable polymeric material (or a polymer blend or a copolymer) between adjacent staple-forming cavities at selected locations on the tissue-contacting surface 302. The attachment features 316b, 316c, 316d, as well as other attachment features formed on the tissue-contacting surface 302, can be formed in a similar manner and are not shown in detail.

FIG. 15 also illustrates that the adjunct material 310 (which is shown partially in FIG. 14) has a mating feature 318a configured to be received within the pocket 316a. The mating feature 318a can be in the form of an expandable (e.g., umbrella-like) mating feature extending through a thickness of the adjunct 310 and a portion of which expands upon being inserted into the pocket 316a. The pocket 316a and the mating feature 318a are configured to mate such that, when staples are ejected from a cartridge and formed against the staple-forming cavities, the mating features 318a are caused to be disengaged from the pocket 316a.

As shown in FIG. 15, the mating feature 318a can be associated with the adjunct such that its top portion 319 seats on one side above the surface of the adjunct 310, its mid-portion 321 penetrates through the adjunct's surface and extends toward the opposite side of the adjunct that comes in contact with the anvil's tissue-contacting surface 302, and its expandable bottom portion 323 is disposed on the opposite side of the adjunct, within the pocket 316a. The expandable portion 323 of the mating feature 318a can have one or more portions (e.g., arms, wings, prongs, snaps, etc.) that are configured to expand when load is applied to the top portion 319.

In use, the adjunct material 310 is brought in proximity to the tissue-contacting surface 302 and force can be applied to the adjunct material 310 to cause the mating feature 318a to be received within the pocket 316a such that the expandable portion 323 is received within the pocket 316a and expands to thereby releasably retain the adjunct 310 over the tissue-contacting surface 302. It should be appreciated that the mating feature 318a can have other configurations that allow this feature to be used to releasably retain the adjunct on the jaw. The adjunct's mating features can have a changeable configuration, e.g., such that at least a portion of the feature expands, as the exemplary mating feature 318a in FIG. 15. As another variation, the mating feature can be in the form of a hook or other non-expandable feature configured to be received within a recess in a jaw. The load can be applied to the adjunct 310 manually, or using a loader or applicator member which can be removably coupled to the end effector or removably coupled to the adjunct 310. In some embodiments, the adjunct 310 can have an applicator (e.g., in the form of a frame of a suitable configuration disposed over the adjunct) for applying load thereto to be coupled to the adjunct 310. During a surgical procedure, such applicator can be utilized to cause the adjunct 310 to be releasably retained over the jaw.

FIG. 14 shows that, besides the attachment features 316a, 316b, 316c, 316d, the tissue-contacting surface 302 also attachment features 320a, 320b, 320c, 320d formed at a mid-portion 300m of the anvil 300. The tissue-contacting surface 302 also has attachment features 322a, 322b, 322c, 322d formed at a proximal portion 300p of the anvil 300, the locations of which are shown schematically in FIG. 14 as these features are obscured by the adjunct 310. Additionally, the tissue-contacting surface 302 has proximal-most attachment features 324a, 324b (obscured by the adjunct 310), which locations are shown in FIG. 14. The attachment features 324a, 324b are disposed at opposite sides of an anvil knife channel 308 extending between distal and proximal ends 300d, 300p of the anvil 300.

The mid-portion attachment features 320a, 320b, 320c, 320d and the proximal attachment features 322a, 322b, 322c, 322d are arranged in two respective rows generally perpendicular to the longitudinal axis A3 of the anvil 300. As in this example, the attachment features can be located symmetrically with respect to the anvil knife channel 108. Regardless of its specific location, each of the attachment features is configured to releasably mate with at least one mating feature formed on the adjunct material. Thus, FIG. 14 schematically shows that the proximal attachment features 322a, 322b, 322c, 322d (obscured in FIG. 14) are configured to mate with respective adjunct's mating feature collectively indicated as features 326. These mating features can be configured similar to the feature 318a shown in FIG. 15, or in another way.

It should be appreciated that the attachment features in FIG. 14 are shown to form three rows by way of example only, as attachment features can be formed on a tissue-contacting surface of a jaw at any desired locations, so as to form various patterns. Also, eight attachment features are shown by way of example, as any number of the attachment features can be formed on the jaw's tissue-contacting surface. Furthermore, although the anvil 300 is shown in FIGS. 14 and 15, in some implementations, features similar to those shown in FIGS. 14 and 15 can be formed on a cartridge body of an end effector. Also, the cartridge body and the anvil of an end effector can have respective adjuncts releasably coupled thereto via different techniques. For example, the cartridge body can have extension elements with attachment features as shown in FIGS. 6-8 (and in FIGS. 10 and 11), whereas the anvil can have openings or pockets as shown in FIGS. 14 and 15, or vice versa.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An end effector for a surgical instrument, comprising:
   a first jaw having a cartridge body, the cartridge body having on a tissue-contacting surface thereof a plurality of staple cavities configured to seat staples therein, the first jaw having a generally rectangular nominal perimeter defining a regular perimeter around outer rows of the plurality of staple cavities;
   a second jaw having an anvil with a plurality of staple forming cavities formed on a tissue-contacting surface thereof, wherein at least one of the first and second jaws is movable relative to the other between open and closed positions, the second jaw having a generally rectangular nominal perimeter opposed to the nominal perimeter of the first jaw;
   a plurality of attachment features formed on at least one jaw of the first and second jaws on extension elements extending beyond the nominal perimeter of the at least one jaw such that each of the extension elements has at least one attachment feature formed thereon; and
   an adjunct material having a shape complementary to at least one of the first and second jaws and being configured to releasably mate with the attachment features;
   wherein the adjunct material comprises at least one mating feature that is complementary to the at least one attachment feature and is configured to releasably mate with the at least one attachment feature, and
   wherein the at least one attachment feature comprises a projection extending perpendicular to a longitudinal axis of the at least one jaw from the corresponding extension element formed on the at least one jaw, and wherein the at least one mating feature comprises a through opening formed in the adjunct material and configured to receive the projection therein.

2. The end effector of claim 1, wherein the extension elements are formed along at least one of the long sides of the at least one jaw.

3. The end effector of claim 1, wherein the extension elements extend in a plane of the at least one jaw that is parallel to a tissue contacting surface of the at least one jaw.

4. The end effector of claim 1, wherein the extension elements are formed integrally with the at least one jaw.

5. The end effector of claim 1, wherein the extension elements comprise first extension elements formed on the first jaw and second extension elements formed on the second jaw.

6. The end effector of claim 5, wherein the first and second extension elements are formed such that, when the end effector is in the closed position, the first extension elements extend beyond the nominal perimeter of the second jaw and the second extension elements extend beyond the nominal perimeter of the first jaw.

7. The end effector of claim 5, wherein the first extension elements are staggered with respect to the second extension elements.

8. The end effector of claim 1, wherein the other one of the first and second jaws has at least one second attachment feature formed thereon that is different from each of the attachment features formed on the extension elements extending beyond the nominal perimeter of the at least one jaw, the second attachment feature being configured to mate with a second adjunct material to releasably retain the second adjunct material on the other jaw.

9. The end effector of claim 1, wherein the cartridge body is a removable and replaceable cartridge body.

10. An end effector for a surgical instrument, comprising:
    a first jaw having a cartridge body, the cartridge body having on a tissue-contacting surface thereof a plurality of staple cavities configured to seat staples therein, the first jaw having a generally rectangular nominal perimeter defining a regular perimeter around outer rows of the plurality of staple cavities;
    a second jaw having an anvil with a plurality of staple forming cavities formed on a tissue-contacting surface thereof, wherein at least one of the first and second jaws is movable relative to the other between open and closed positions, the second jaw having a generally rectangular nominal perimeter opposed to the nominal perimeter of the first jaw;

a plurality of attachment features formed on at least one jaw of the first and second jaws on extension elements extending beyond the nominal perimeter of the at least one jaw such that each of the extension elements has at least one attachment feature formed thereon; and an adjunct material having a shape complementary to at least one of the first and second jaws and being configured to releasably mate with the attachment features;

wherein the at least one attachment feature comprises a recess formed in the corresponding extension element formed on the at least one jaw.

11. The end effector of claim 10, wherein the extension elements are formed along at least one of the long sides of the at least one jaw.

12. The end effector of claim 10, wherein the extension elements extend in a plane of the at least one jaw that is parallel to a tissue contacting surface of the at least one jaw.

13. The end effector of claim 10, wherein the extension elements comprise first extension elements formed on the first jaw and second extension elements formed on the second jaw.

14. The end effector of claim 10, wherein the other one of the first and second jaws has at least one second attachment feature formed thereon that is different from each of the attachment features formed on the extension elements extending beyond the nominal perimeter of the at least one jaw, the second attachment feature being configured to mate with a second adjunct material to releasably retain the second adjunct material on the other jaw.

15. An end effector for a surgical instrument, comprising:
a first jaw having a cartridge body, the cartridge body having on a tissue-contacting surface thereof a plurality of staple cavities configured to seat staples therein, the first jaw having a generally rectangular nominal perimeter defining a regular perimeter around outer rows of the plurality of staple cavities;

a second jaw having an anvil with a plurality of staple forming cavities formed on a tissue-contacting surface thereof, wherein at least one of the first and second jaws is movable relative to the other between open and closed positions, the second jaw having a generally rectangular nominal perimeter opposed to the nominal perimeter of the first jaw;

a plurality of attachment features formed on at least one jaw of the first and second jaws on extension elements extending beyond the nominal perimeter of the at least one jaw such that each of the extension elements has at least one attachment feature formed thereon; and an adjunct material having a shape complementary to at least one of the first and second jaws and being configured to releasably mate with the attachment features;

wherein the at least one attachment feature comprises a through opening formed in the corresponding extension element formed on the at least one jaw.

16. The end effector of claim 15, wherein the extension elements are formed along at least one of the long sides of the at least one jaw.

17. The end effector of claim 15, wherein the extension elements extend in a plane of the at least one jaw that is parallel to a tissue contacting surface of the at least one jaw.

18. The end effector of claim 15, wherein the extension elements comprise first extension elements formed on the first jaw and second extension elements formed on the second jaw.

19. The end effector of claim 15, wherein the other one of the first and second jaws has at least one second attachment feature formed thereon that is different from each of the attachment features formed on the extension elements extending beyond the nominal perimeter of the at least one jaw, the second attachment feature being configured to mate with a second adjunct material to releasably retain the second adjunct material on the other jaw.

* * * * *